United States Patent [19]

André et al.

[11] Patent Number: 4,988,815

[45] Date of Patent: Jan. 29, 1991

[54] 3-AMINO OR 3-NITRO QUINOLINE COMPOUNDS WHICH ARE INTERMEDIATES IN PREPARING 1H-IMIDAZO[4,5-C]QUINOLINES

[75] Inventors: Jean-Denis André, Pithiviers; Daniel Lagain, Dadonville, both of France

[73] Assignee: Riker Laboratories, Inc., St. Paul, Minn.

[21] Appl. No.: 426,677

[22] Filed: Oct. 26, 1989

[51] Int. Cl.$^5$ .......................................... C07D 215/38
[52] U.S. Cl. .................................................. 546/159
[58] Field of Search ......................................... 546/159

[56] References Cited

U.S. PATENT DOCUMENTS 4,689,338 8/1987 Gerster ................................. 546/82
4,698,348 10/1987 Gerster ................................. 546/82

FOREIGN PATENT DOCUMENTS 242806 2/1987 German Democratic Rep. ... 546/82

OTHER PUBLICATIONS

Chem. Ber., 1927, 60, 1108 (Koller).
J. Heterocyclic Chem., 1988, 25, 857 (Kappe et al.).
Chem. Ber., 1918, 51, 1500 (Gabriel).
J. Med. Chem. 1975, 18, 726 (Buckle et al.).
J. Org. Chem., 1910, 15, 1278 (Bachman et al.).
J. Med. Chem. 1968, 11, 87 (Jain et al.).
Chem. Abs. 1976, 85, 94362z (Baranov et al.).
J. Heterocyclic Chem. 1981, 18, 1537 (Berenyi et al.).

*Primary Examiner*—Mary C. Lee
*Assistant Examiner*—Zinna Northington-Davis
*Attorney, Agent, or Firm*—Donald M. Sell; Walter N. Kirn; Robert W. Sprague

[57] ABSTRACT

A process for the preparation of 1-substituted, 4-substituted-1H-imidazo[4,5-c]quinolines, intermediates in the preparation of such compounds, and processes for the preparation of such intermediates.

6 Claims, No Drawings

3-AMINO OR 3-NITRO QUINOLINE COMPOUNDS WHICH ARE INTERMEDIATES IN PREPARING 1H-IMIDAZO[4,5-C]QUINOLINES

BACKGROUND OF THE INVENTION

1. Field of the Invention

This invention pertains to processes for the preparation of 1H-imidazo[4,5-c]quinolines. More particularly, this invention pertains to processes for the preparation of 1-substituted,4-substituted-1H-imidazo-[4,5-c]quinolines. In another aspect, this invention pertains to intermediates in the preparation of 1H-imidazo[4,5-c]quinolines, and to processes for the preparation of such intermediates.

2. Description of the Related Art

The synthesis of 4-substituted 1H-imidazo[4,5-c]quinolines via 4-chloro-1H-imidazo[4,5-c]quinolines has been reported in U.S. Pat. Nos. 4,689,338 and 4,698,348 (Gerster). The synthetic scheme used therein involves first condensing a quinoline with amine functionality at the 3- and 4-position with a trialkyl orthoester or a functional equivalent thereof to form the 1H-imidazo[4,5-c]quinoline ring system, followed by introduction of a 4-chloro substituent by oxidizing the 5-nitrogen and reacting the resulting N-oxide with a chlorinating agent. Replacement of the 4-chloro substituent with a selected nucleophile such as ammonia then affords the desired 4-substituted-1H-imidazo[4,5-c]quinoline, e.g., the corresponding 1H-imidazo[4,5-c]quinolin-4-amine when ammonia is employed as the nucleophile.

SUMMARY OF THE INVENTION

This invention provides a process for preparing a 1H-imidazo[4,5-c]quinoline of Formula I below:

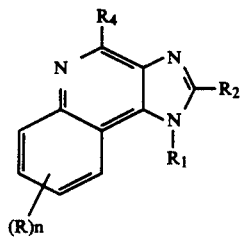

wherein $R_1$ is selected from the group consisting of: straight chain or branched chain alkyl of one to about 10 carbon atoms; straight chain or branched chain alkenyl of 3 to about 10 carbon atoms wherein the olefinic unsaturation is at least one carbon atom removed from the 1-nitrogen; substituted straight chain or branched chain alkenyl of 3 to about 10 carbon atoms wherein the olefinic unsaturation is at least one carbon atom removed from the 1-nitrogen, and wherein the substituent is selected from the group consisting of lower alkyl, cycloalkyl of 3 to about 6 carbon atoms, and cycloalkyl of 3 to about 6 carbon atoms substituted by lower alkyl; substituted straight chain or branched chain alkyl of one to about 10 carbon atoms, wherein the substituent is selected from the group consisting of lower alkyl, cycloalkyl of 3 to about 6 carbon atoms substituted by lower alkyl; hydroxyalkyl of one to about 6 carbon atoms; and dihydroxyalkyl of one to about 6 carbon atoms;

$R_2$ is selected from the group consisting of: hydrogen; straight chain or branched chain alkyl containing one to about eight carbon atoms; benzyl, (phenyl)ethyl and phenyl, the benzyl, (phenyl)ethyl or phenyl substituent being optionally substituted on the benzene ring by one or two moieties independently selected from the group consisting of lower alkyl, lower alkoxy and halogen, with the proviso that when the benzene ring is substituted by two such moieties, then the moieties together contain no more than 6 carbon atoms;

$R_4$ is selected from the group consisting of amino, (lower)alkylamino, di(lower)alkylamino, lower alkoxy, phenylthio, lower alkylthio, and morpholino; and each R is independently selected from the group consisting of lower alkoxy, halogen, and lower alkyl, and n is an integer from zero to 2, with the proviso that if n is 2, then said R groups together contain no more than 6 carbon atoms; or a pharmaceutically acceptable acid addition salt thereof, which process comprises (1) nitrating a compound of Formula II

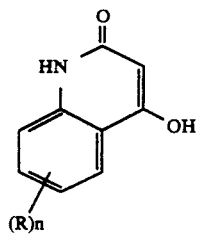

wherein R and n are as defined above, to provide a compound of Formula III

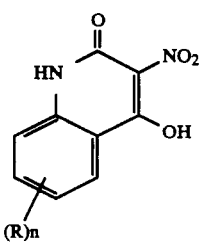

wherein R and n are as defined above, (2) chlorinating the product of step (1) with a suitable chlorinating agent to provide a compound of Formula IV

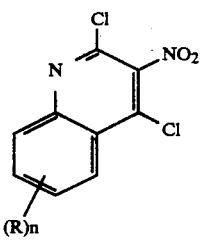

wherein R and n are as defined above, (3) reacting the product of step (2) at the 4-position by reaction with a compound of the formula $R_1NH_2$ wherein $R_1$ is as defined above, to provide a compound of Formula V

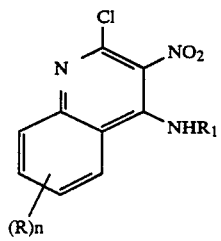

wherein R, n, and $R_1$ are as defined above, (4) reducing the product of step (3) to provide a compound of Formula VI

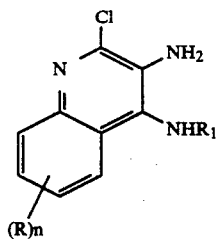

wherein R, n, and $R_1$ are as defined above, (5) reacting the product of step (4) with a compound of the formula $R_2C(O\text{-Alkyl})_3$ or a compound of the formula $R_2CO_2H$ or a mixture thereof, wherein $R_2$ is as defined above and each alkyl is independently selected from the group consisting of straight chain or branched chain alkyl of 1 to about 8 carbon atoms to provide compound of Formula VII

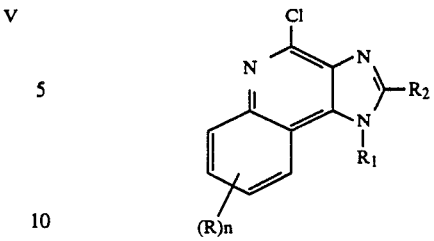

wherein R, n, $R_1$, and $R_2$ are as defined above, (6) reacting the product of step (5) with a compound of the formula $R_4H$ wherein $R_4$ is as defined above, or with a compound of the formula $R_4M$, wherein $R_4$ is as defined above and M is an alkali metal, in an inert solvent to provide a compound of Formula I.

This invention also provides singular reaction steps from the above-described overall process as well as combinations of two or more sequential steps of the above-described overall process.

The compounds prepared by the process of the invention are known bronchodilators or antiviral agents, depending on the nature of the $R_4$ substituent.

This invention also provides novel intermediates, compounds of Formula V an Formula VI in particular, useful in the preparation of the 1H-imidazo[4,5-c]quinolines described above.

DETAILED DESCRIPTION OF THE INVENTION

For purposes of the instant specification and claims, the term "lower" when used in conjunction with "alkyl" or "alkoxy" designates straight chain or branched chain substituents containing 1 to about 4 carbon atoms.

The process of the invention is set forth in the Reaction Scheme below. The starting compound of Formula II has functionality in place in the 2-position. As discussed in detail below, the functionality at the 2-position of a compound of Formula II is carried through the synthesis and ultimately converted to a desired 4-substituent in a 1H-imidazo[4,5-c]quinoline.

REACTION SCHEME

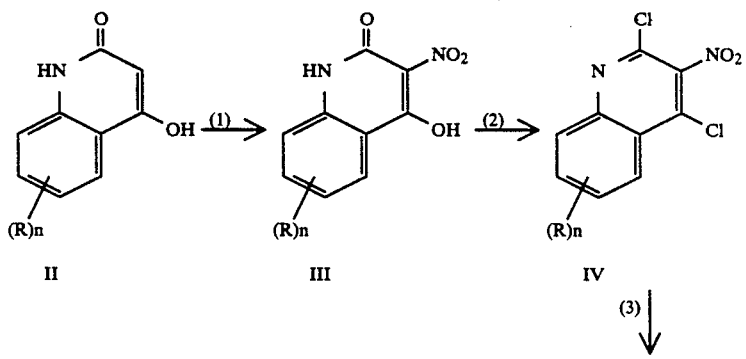

-continued
REACTION SCHEME

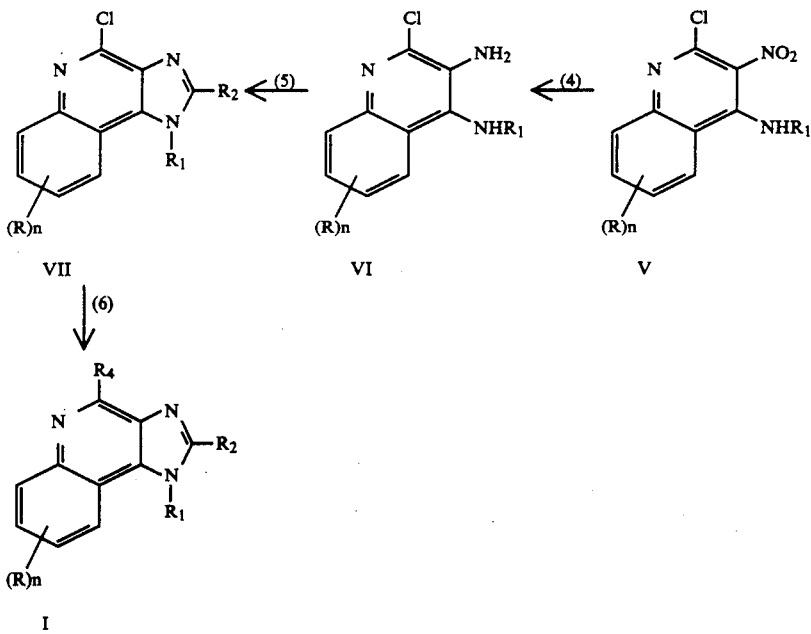

The unsubstituted compound of Formula II, 4-hydroxy-2(1H)-quinolinone, is a known, commercially available compound, and other compounds of Formula II can be prepared therefrom by methods known to those skilled in the art. For example, *Chem. Ber.*, 1927, 60, 1108 (Kohler), discloses the preparation of 7-chloro-4-hydroxy-2(1H)-quinolinone, and *J. Heterocyclic Chem.* 1988, 25, 857 (Kappe et al.) discloses 4-hydroxy-2(1H)-quinolinones with, e.g., 5,8-dichloro substitution, 6,8-dichloro substitution, and 7-chloro-8-methoxy substitution. The disclosure of the above-cited articles is incorporated herein by reference, In step (1) a compound of Formula II is nitrated at the 3-position using conventional nitration methods. It is known to those skilled in the art, however, that nitration is not necessarily selective. For example, depending on the particular R substituents in a compound of Formula II and the particular conditions employed, nitration might occur on the benzo ring of a compound of Formula II. Those skilled in the art, however, are able to select appropriate conditions that will afford a compound of Formula III. Preferred conditions involve the use of mild heating (e.g., at about 40° C.) with acetic acid as the solvent. The unsubstituted compound of Formula III, 4-hydroxy-3-nitro-2(1H)-quinolinone is known and the preparation thereof is disclosed in *Chem. Ber.* 1918, 51, 1500 (Gabriel), the disclosure of which is incorporated herein by reference.

In step (2) the nitrated compound of Formula III is chlorinated with a suitable chlorinating agent such as thionyl chloride, phosgene, oxalyl chloride, phosphorus pentachloride, and the like, or preferably phosphorus oxychloride to provide the dichloride product of Formula IV. The reaction can be carried out in an inert solvent or if appropriate in neat chlorinating agent. Mild heating serves to accelerate the rate of reaction. Preferred conditions involve reaction in neat phosphorus oxychloride with heating at about 100° C. The unsubstituted compound of Formula IV, 2,4-chloro-3-nitroquinoline, is known and the preparation thereof is disclosed in Gabriel cited above.

The product of Formula IV can be isolated if desired, but it is preferred to carry out steps (2) and (3) without isolation of the compound of Formula IV. Such a preferred process involves carrying out the reaction of step (2), careful hydrolysis of unreacted chlorinating agent at a relatively low temperature (e.g., below about 35° C.), separating the organic layer, removing the product of Formula IV from the remaining aqueous layer by extraction with an organic solvent, and using the combined organic extracts as described below in connection with step (3).

In step (3), a compound of Formula IV is substituted at the 4-position by reaction with an excess of a compound of the formula $R_1NH_2$, wherein $R_1$ is as defined above. It is sometimes necessary to use gentle heating (e.g., 50° C.). This reaction proceeds selectively, affording only the 4-substituted product and no detectable amount of the 2-substituted compound. The reaction is run in a solvent comprising a base such as triethylamine or pyridine. When step (3) is run independent of step (2), the reaction can be carried out in a neat basic solvent such as triethylamine. Gentle heating (e.g., at about 70°) is preferred.

In step (4), a compound of Formula V is reduced to afford a compound of Formula VI. This reduction can be carried out by conventional methods such as by electrochemical reduction, by reaction with metals such as zinc, tin, or iron in acid, by reaction with sulfides such as NaHS, by reaction with sodium dihydro(trithio)borate, and by other conventional single step or multistep (e.g., via the hydroxylamine intermediate) methods known to those skilled in the art. Preferred reduction conditions include conventional homogeneous or preferably heterogeneous catalytic hydrogenation conditions. A compound of Formula V is suspended or preferably dissolved in a solvent such as ethanol, ethyl acetate, methanol, isopropyl alcohol, or mixtures thereof with acetic acid, in the presence of a suitable heterogeneous hydrogenation catalyst such as a platinum or rhodium on alumina, palladium on carbon, platinum on carbon, or the like under hydrogen pressure (e.g., 1–5 atm) in a steel bomb. Isopropyl alcohol is the preferred solvent.

In step (5), a compound of Formula VI is reacted with an orthoester or an orthoformate of the formula $R_2C(O\text{-Alkyl})_3$ or a carboxylic acid of the formula $R_2CO_2H$ or a mixture thereof, wherein each alkyl is independently selected from the group consisting of straight chain or branched chain alkyl of 1 to about 8 carbon atoms and $R_2$ is as defined above. The reaction can be run in the absence of solvent or preferably in an inert solvent such as xylene, toluene, and the like, in the presence of a carboxylic acid of the formula $R_2CO_2H$ with sufficient heating (e.g., about 80° C. to about 150° C. depending on the solvent, if any) to drive off any alcohol or water formed as a side product, thereby helping to drive the reaction to completion.

In step (6), a compound of Formula VII is reacted with a compound of the formula $R_4H$, wherein $R_4$ is as defined above. The reaction can be run with heating and under pressure if necessary, and in neat $R_4H$ if such a compound (e.g., morpholine, diethylamine, and various hydroxyalkylamines) is a suitable solvent, or in the presence of a suitable polar solvent such as water or methanol (e.g., commercially available aqueous solutions of ethylamine and other lower alkylamines and di-lower alkylamines, and 15%–20% by weight solutions of ammonia in methanol are suitable). In some instances, such as when $R_4$ is lower alkoxy, phenylthio, or lower alkylthio, it is preferred to run the reaction in the presence of an excess (e.g., several equivalents) of the corresponding alkali metal lower alkoxide, lower alkylthiolate, or phenylthiolate.

The process of the invention provides as a final product a compound of Formula I. Such compounds are disclosed in U.S. Pat. No. 4,698,438 and U.S. Pat. No. 4,689,338 as either bronchodilators or antiviral agents depending on the nature of the substituent $R_4$.

The EXAMPLES below are intended to illustrate the invention, they are not intended to limit the invention.

EXAMPLE 1

4-Hydroxy-3-nitro-2(1H)-quinolinone

Fuming nitric acid (262 mL) was added at about 20° C. to a suspension of 4-hydroxy-2(1H)-quinonlinone (1.0 Kg) in acetic acid (7.57 L). The mixture was heated at 40° C. for 2.5 h. The resulting solution was cooled to about 20° C. and poured into 8 L of water. The resulting mixture was stirred for 20 min, filtered, washed with water until the filtrate was neutral, and dried. The product 4-hydroxy-3-nitro-2(1H)-quinolinone was isolated in 98% yield and showed only one spot upon analysis by thin layer chromatography (silica gel, 20:80 (V/V) chloroform in methanol).

EXAMPLE 2

2,4-Dichloro-3-nitroquinoline

Phosphorous oxychloride (50 mL) was added over a period of 1 hour to a mixture of 4-hydroxy-3-nitro-2(1H)-quinolinone (10 g) and pyridine (10 mL), keeping the temperature below 50° C. The suspension was heated at reflux for 5 h, during which time 40 mL of phosphorus oxychloride was removed by distillation. Cold water was slowly added to the mixture, maintaining temperature below 30° C. The resulting aqueous solution was extracted with chloroform. The extracts were dried over sodium sulfate and concentrated. The solid product 2,4-dichloro-3-nitroquinoline was recrystallized from petroleum ether.

EXAMPLE 3

2-Chloro-N-(2-methylpropyl)-3-nitro-4-quinolinamine

2-Methylpropylamine (0.5 mL) was added to a suspension of 2,4-dichloro-3-nitroquinoline (1 g) and triethylamine (15 mL) at 40° C. over a period of 40 min. The solution was then heated at 70° C. for 1 h. The triethylamine and 2-methylpropylamine were removed by distillation and the residue was slurried for 1 h in aqueous 1N HCl. The solid product 2-chloro-N-(2-methylpropyl)-3-nitro-4-quinolinamine was collected by filtration, washed with water and recrystallized from petroleum ether.

EXAMPLE 4

2-Chloro-$N^4$-(2-methylpropyl)-3,4-quinolinediamine

A solution of 2-chloro-N-(2-methylpropyl)-3-nitro-4-quinolinamine (120 g), acetic acid (300 mL), isopropyl alcohol (300 mL), and 5% platinum on carbon (7.2 g) was allowed to stand at room temperature for 30 h under 2 bars of hydrogen pressure. The resulting solution was filtered, and the solvent was removed from the filtrate at reduced pressure. The residue was dissolved in aqueous hydrochloric acid (1 L, 4N). The product was precipitated by adding this solution to a solution of sodium hydroxide. The precipitate was filtered and washed with water to afford the product 2-chloro-$N^4$-(2-methylpropyl)-3,4-quinolinediamine in 73% yield.

EXAMPLE 5

4-Chloro-1-(2-methylpropyl)-1H-imidazo[4,5-c]quinoline

A solution of 2-chloro-$N^4$-(2-methylpropyl)-3,4-quinolinediamine (3 g) in triethylorthoformate (2.8 g) was heated at 80° C. for 15 h. The resulting solution was cooled to ambient temperature and 20 mL of chloroform was added. The solution was washed with water. The product 4-chloro-1-(2-methylpropyl)-1H-imidazo[4,5-c]-quinoline was obtained by concentrating the solution.

EXAMPLE 6

1-(2-Methylpropyl)-1H-imidazo[4,5-c]quinolin-4-amine

A solution of 4-chloro-1-(2-methylpropyl)-1H-imidazo[4,5-c]quinoline (0.86 g) in 7 g of a methanol solution containing 20% by weight of ammonia was placed in a steel bomb for 20 h at 150° C. After cooling to 20° C., the solid formed was collected by filtration and washed with methanol. The crude product 1-(2-methylpropyl)-1H-imidazo[4,5-c]quinolin-4-amine was recystallized from N,N-dimethylformamide.

EXAMPLE 7

2,4-Dichloro-3-nitroquinoline

Phosphorus oxychloride (614 g, 4 eq) was added to a mixture of 4-hydroxy-3-nitro-2(1H)-quinolinone (206.16 g), triethylamine (152 g, 1.5 eq) and toluene (620 mL) such that the temperature remained below 50° C. The suspension was then heated at 110° C. for 11 h. The resulting suspension was cooled to room temperature and poured into 1.7 L of water at a rate such that the temperature remained below 50° C. The organic phase was removed, and the aqueous phase was extracted with toluene (2×250 mL). The organics were combined and washed with water (3×250 mL). The solvent was removed at reduced pressure to afford a product 2,4-dichloro-3-nitroquinoline that showed one spot when analyzed by thin layer chromatography (silica gel, 1:1 (V/V) methanol in chloroform) in 70% assay-corrected yield.

EXAMPLE 8

2-Chloro-N-(2-methylpropyl)-3-nitro-4-quinolinamine

A mixture of 2,4-dichloro-3-nitroquinoline (100 g) and N,N-dimethylformamide (180 mL) was stirred, and triethylamine (42 g, 4 eq) was added dropwise, followed by dropwise addition of 2-methylpropylamine (21.5 g, 0.7 eq). The mixture was stirred at room temperature until the reaction was completed as determined by gas chromatography. Aqueous hydrochloric acid (250 mL, 4N) was added with stirring. The resulting mixture was stirred and cooled to about 0° C. to precipitate the product. The precipitate was filtered, washed with water, and dried at reduced pressure to afford the product 2-chloro-N-(2-methylpropyl)-3-nitro-4-quinolinamine in about 90% yield.

EXAMPLE 9

4-Chloro-1-(2-methylpropyl)-1H-imidazo[4,5-c]quinoline

A suspension of 2-chloro-$N^4$-(2-methylpropyl)-3,4-quinolinediamine (35 g) and triethylorthoformate (52.3 g, 2.5 eq) was heated at 145° C. for 10 h, during which time ethanol was removed by distillation. The resulting mixture was cooled to room temperature and the solid was removed by filtration. The solid was dissolved in hydrochloric acid (100 mL, 4N). The resulting solution was added to a solution of sodium hydroxide. The precipitate was filtered and washed with water to afford the product 4-chloro-1-(2-methylpropyl)-1H-imidazo[4,5-c]quinoline in 92% yield.

EXAMPLE 10

1-(2-Methylpropyl)-1H-imidazo[4,5-c]quinolin-4-amine

A mixture of 4-chloro-1-(2-methylpropyl)-1H-imidazo[4,5-c]quinoline (66 g), methanol (266 mL) and ammonia (46.2 g) was placed in a steel bomb and heated at 150° C. for 8 h. The resulting mixture was filtered, and the solid was washed with water and dried to afford the product 1-(2-methylpropyl)-1H-imidazo[4,5-c]quinolin-4-amine in 70% yield.

EXAMPLE 11

Alternate Preparation of
2-Chloro-N-(2-methylpropyl)-3-nitro-4-quinolinamine

Phosphorous oxychloride (3.067 kg, 4.0 eq) was added to a suspension of 4-hydroxy-3-nitro-2(1H)-quinolinone (1.031 kg), triethylamine (1.045 L) and toluene (3.6 L) over a period of 4 h, during which time the temperature of the suspension was maintained below 50° C. The resulting solution was then heated at reflux (95° C. to 100° C.) for 11 h. After reflux the mixture was cooled to 25° C. and poured into water (6.5 L) over a period of 1.5 h such that the temperature remained below 35° C. The organic phase was separated, and the aqueous phase was extracted with toluene (2×1 L). The combined organic phase was washed with water (3×1 L) and filtered. Triethylamine (428 g) was added to the filtrate, and 2-methylpropylamine (262.8 g) was added to the resulting solution. The solution containing the 2-methylpropylamine was heated at 50° C. for 3 h, after which time additional 2-methylpropylamine (42 g) was added and the reaction stirred for 3 h. Hydrochloric acid (37% aqueous solution, 1.41 L) was added. The suspension was cooled to room temperature, and the precipitated product was collected by filtration, slurried in cold acetone (3 L), and neutralized with sodium hydroxide (4.5 L of 20% by weight aqueous solution). The precipitated product was filtered, washed with water, and dried to afford a yellow solid product (2-chloro-N-(2-methylpropyl)-3-nitro-4-quinolinamine (98% pure by gas chromatography) in 56% overall yield.

EXAMPLE 12

1-[(2-Chloro-3-nitro-4-quinolinyl)amino]-2-methyl-2-propanol

A solution of 2,4-dichloro-3-nitroquinoline (11.5 g from EXAMPLE 7), N,N-dimethylformamide (25 mL) and triethylamine (1 eq) was prepared. To this solution, 1-amino-2-methyl-2-propanol (3.6 g) was added dropwise with stirring at room temperature, during which time the reaction temperature increased to 35° C. After the addition was complete the reaction was heated at 55° C. for 1 h, then cooled to room temperature. Water (50 mL) was added, and the resulting suspension was filtered. The solid product was washed with water and dried to afford 12 g of 1-[(2-chloro-3-nitro-4-quinolinyl)amino]-2-methyl-2-propanol.

EXAMPLE 13

1-[(3-Amino-2-chloro-4-quinolinyl)amino]-2-methyl-2-propanol

A solution of 1-[2-chloro-3-nitro-4-quinolinyl)amino]-2-methyl-2-propanol (10 g from EXAMPLE 12), isopropyl alcohol (100 mL), and 5% Pt/C (0.4 g) was placed in a steel bomb and allowed to stand under hydrogen pressure (2 atm) for 8 h. The catalyst was filtered and washed with ethanol. The solvent was removed from the combined filtrate under reduced pressure, and the resulting material was dissolved in aqueous hydrochloric acid (4N, 100 mL). The resulting solution was filtered, the filtrate was made basic with aqueous sodium hydroxide and extracted with chloroform (3×30 mL). The solvent was evaporated from the combined extracts under reduced pressure to afford 7 g of 1-[(3-amino-2-chloro-4-quinolinyl)amino]-2-methyl-2-propanol.

EXAMPLE 14

4-Chloro-α,α-dimethyl-1H-imidazo[4,5-c]quinoline-1-ethanol

A suspension of 1-[(3-amino-2-chloro-4-quinolinyl)amino]-2-methyl-2-propanol (5 g from EXAMPLE 13) in xylene (50 mL) and triethylorthoformate (5 mL) was heated at 80° C. until no starting material remained as determined by thin layer chromatography. The resulting solution was cooled, and the precipitated product was isolated by filtration and washed with xylene (3×10 mL).

EXAMPLE 15

1-Amino-2-methyl-2-propanol

Methanol (32.5 L, 25.7 Kg) in a 10-gallon glass-lined reactor was cooled to 7° C. Anhydrous liquid ammonia, (6.0 Kg, 12.6 eq) was added keeping the temperature below 25° C. The solution was cooled to 7° C. and isobutylene oxide (2.02 Kg, 28.0 mol, 1 eq) was added in one portion (no exotherm was detected). The solution was stirred 4 h at 7° C., then 64 h at about 20° C. The solution was then slowly heated to 60° C. over a period of 2–3 hours, venting the ammonia off with an aspirator. Excess methanol was then distilled off at 65°–70° C., and the product was fractionally distilled at atmospheric pressure. The third fraction (head temp. 118°–160°, pot temp. 140°–200°) afforded 1.69 Kg (67.9%) of 1-amino-2-methyl-2-propanol, 98.3% pure by GC.

The invention claimed is:

1. A compound of the formula

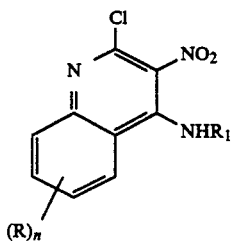

wherein

R$_1$ is selected from the group consisting of: straight chain or branched chain alkyl of one to about 10 carbon atoms; straight chain or branched chain alkenyl of 3 to about 10 carbon atoms wherein the olefinic unsaturation is at least one carbon atom removed from the 1-nitrogen; substituted straight chain or branched chain alkenyl of 3 to about 10 carbon atoms wherein the olefinic unsaturation is at least one carbon atom removed from the 1-nitrogen, and wherein the substituent is selected from the group consisting of lower alkyl, cycloalkyl of 3 to about 6 carbon atoms, and cycloalkyl of 3 to about 6 carbon atoms substituted by lower alkyl; substituted straight chain or branched chain alkyl of one to about 10 carbon atoms, wherein the substituent is selected from the group consisting of lower alkyl, cycloalkyl of 3 to about 6 carbon atoms, and cycloalkyl of 3 to about 6 carbon atoms substituted by lower alkyl; hydroxyalkyl of one to about 6 carbon atoms; and dihydroxyalkyl of one to about 6 carbon atoms;

each R is independently selected from the group consisting of lower alkoxy, halogen, and lower alkyl, n is an integer from zero to 2, with the proviso that if n is 2, then said R groups together contain no more than 6 carbon atoms.

2. A compound according to claim 1, wherein R$_1$ is 2-methylpropyl and n is zero.

3. A compound according to claim 1, wherein R$_1$ is 2-hydroxy-2-methylpropyl and n is zero.

4. A compound of the formula

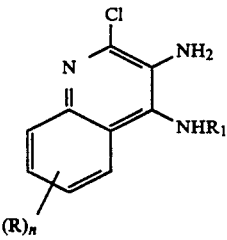

wherein

R$_1$ is selected from the group consisting of: straight chain or branched chain alkyl of one to about 10 carbon atoms; straight chain or branched chain alkenyl of 3 to about 10 carbon atoms wherein the olefinic unsaturation is at least one carbon atom removed from the 1-nitrogen; substituted straight chain or branched chain alkenyl of 3 to about 10 carbon atoms wherein the olefinic unsaturation is at least one carbon atom removed from the 1-nitrogen, and wherein the substituent is selected from the group consisting of lower alkyl, cycloalkyl of 3 to about 6 carbon atoms, and cycloalkyl of 3 to about 6 carbon atoms substituted by lower alkyl; substituted straight chain or branched chain alkyl of one to about 10 carbon atoms, wherein the substituent is selected from the group consisting of lower alkyl, cycloalkyl of 3 to about 6 carbon atoms, and cycloalkyl of 3 to about 6 carbon atoms substituted by lower alkyl; hydroxyalkyl of one to about 6 carbon atoms; or dihydroxyalkyl of one to about 6 carbon atoms;

each R is independently selected from the group consisting of lower alkoxy, halogen, and lower alkyl, n is an integer from zero to 2, with the proviso that if n is 2, then said R groups together contain no more than 6 carbon atoms.

5. A compound according to claim 4, wherein R$_1$ is 2-methylpropyl and n is zero.

6. A compound according to claim 4, wherein R$_1$ is 2-hydroxy-2-methylpropyl and n is zero.

* * * * *